(12) United States Patent
Humayun et al.

(10) Patent No.: US 10,849,788 B2
(45) Date of Patent: Dec. 1, 2020

(54) POLYMER SUBSTRATE RETINAL PATCH COATED WITH ADHESIVES

(71) Applicant: University of Southern California, Los Angeles, CA (US)

(72) Inventors: Mark S. Humayun, Glendale, CA (US); Aldo Oregon, Los Angeles, CA (US); Yi Zhang, Los Angeles, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 435 days.

(21) Appl. No.: 15/074,909

(22) Filed: Mar. 18, 2016

(65) Prior Publication Data

US 2016/0271290 A1 Sep. 22, 2016

Related U.S. Application Data

(60) Provisional application No. 62/135,392, filed on Mar. 19, 2015.

(51) Int. Cl.
*A61F 9/007* (2006.01)
*A61L 27/22* (2006.01)
*A61L 27/24* (2006.01)
*A61L 27/18* (2006.01)

(52) U.S. Cl.
CPC .......... *A61F 9/00727* (2013.01); *A61L 27/18* (2013.01); *A61L 27/222* (2013.01); *A61L 27/225* (2013.01); *A61L 27/227* (2013.01); *A61L 27/24* (2013.01); *A61L 2430/16* (2013.01)

(58) Field of Classification Search
CPC .................. A61F 9/00727; A61F 9/007; A61F 2002/30448; A61B 2220/005; A61B 17/085
USPC ................................ 606/215, 216, 213, 151
See application file for complete search history.

(56) References Cited

U.S. PATENT DOCUMENTS

| | | | |
|---|---|---|---|
| 2005/0182443 A1* | 8/2005 | Jonn | A61B 17/085 606/213 |
| 2008/0140192 A1* | 6/2008 | Humayun | A61L 24/001 623/6.11 |
| 2011/0021965 A1* | 1/2011 | Karp | A61F 2/0077 602/54 |
| 2012/0142603 A1* | 6/2012 | Markland | A61L 27/18 514/17.7 |
| 2013/0012988 A1* | 1/2013 | Blume | A61B 17/085 606/215 |

* cited by examiner

*Primary Examiner* — Diane D Yabut
*Assistant Examiner* — Majid Jamialahmadi
(74) *Attorney, Agent, or Firm* — Brooks Kushman P.C.

(57) ABSTRACT

Several embodiments disclosed herein relate to compositions and methods for treating or repairing damage to ocular tissue. In particular, several embodiments relate to patches that interact, e.g., by way of an adhesive, with damaged retinal tissue to repair or mend a hole, tear or detachment of the retina from underlying ocular tissue. Still additional embodiments relate to self-assembling patches.

23 Claims, 8 Drawing Sheets

Patch with an adhesive coating on one side

Patch with patterned adhesive coating on one side

Patch with an adhesive coating on both sides

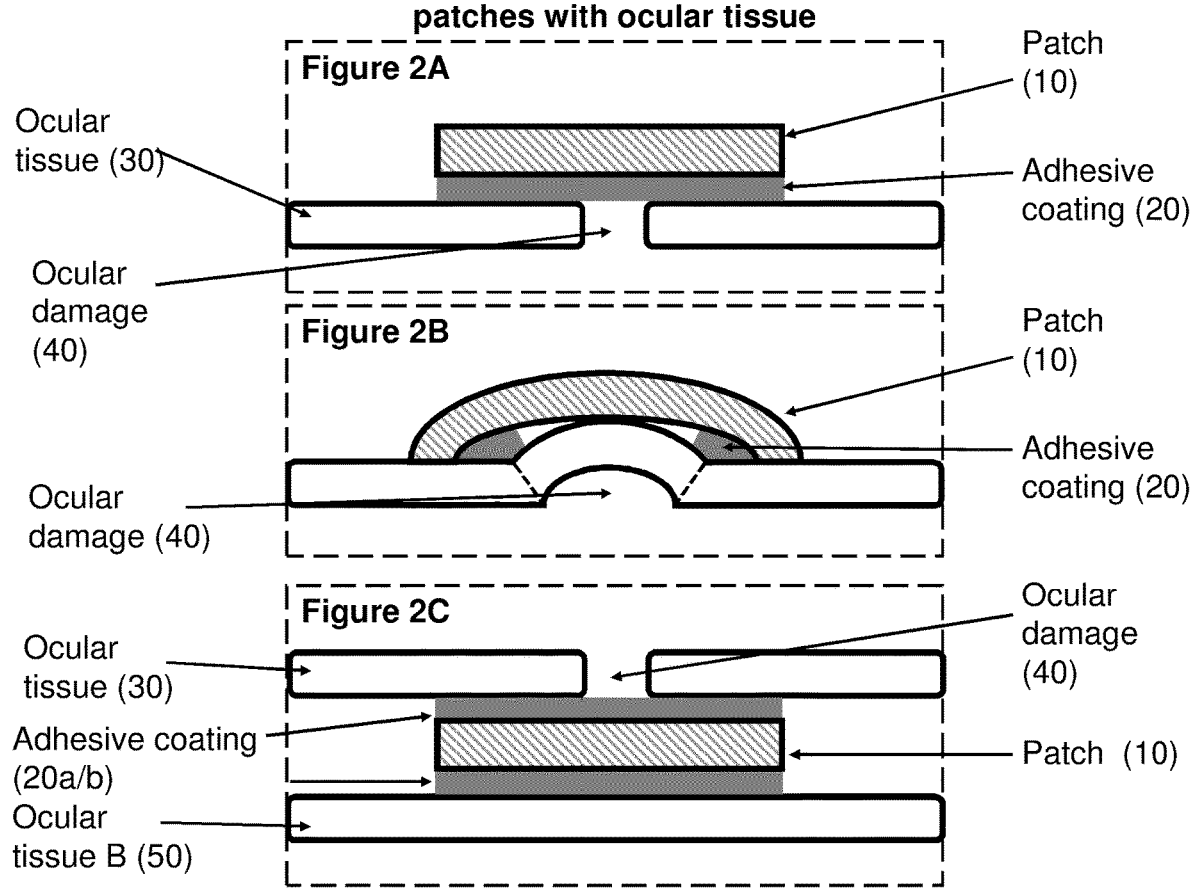

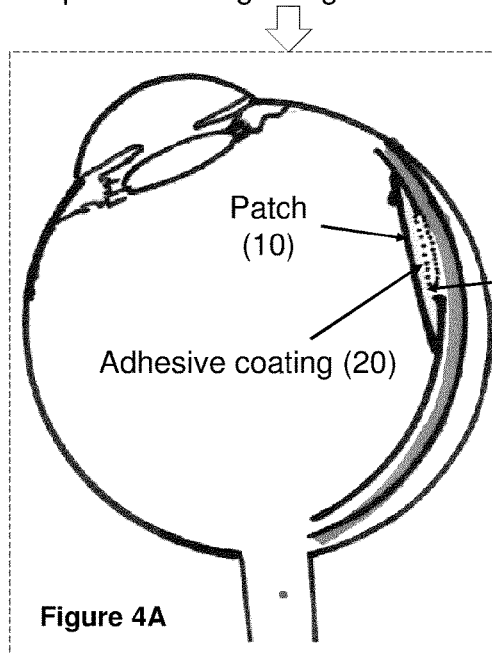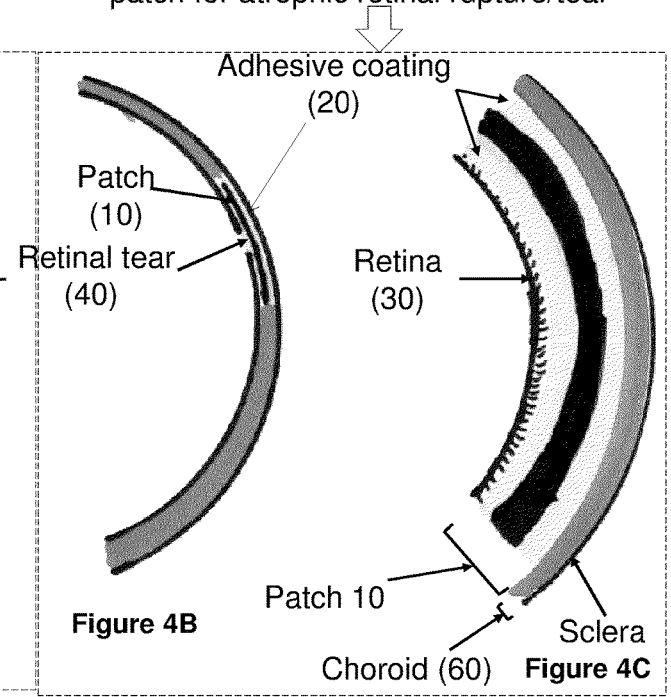
Placement of the patch for retinal ruptures/tear and detachment (Cross sectional views)

Image of a retinal tear in a cadaver porcine eye

Image of placement of a patch device near the retinal tear in a cadaver porcine eye Patch (10) attached or adhered to the retinal tear (subretinal or supraretinal) (40)

Image of placement of the patch device attached to in a cadaver porcine eye

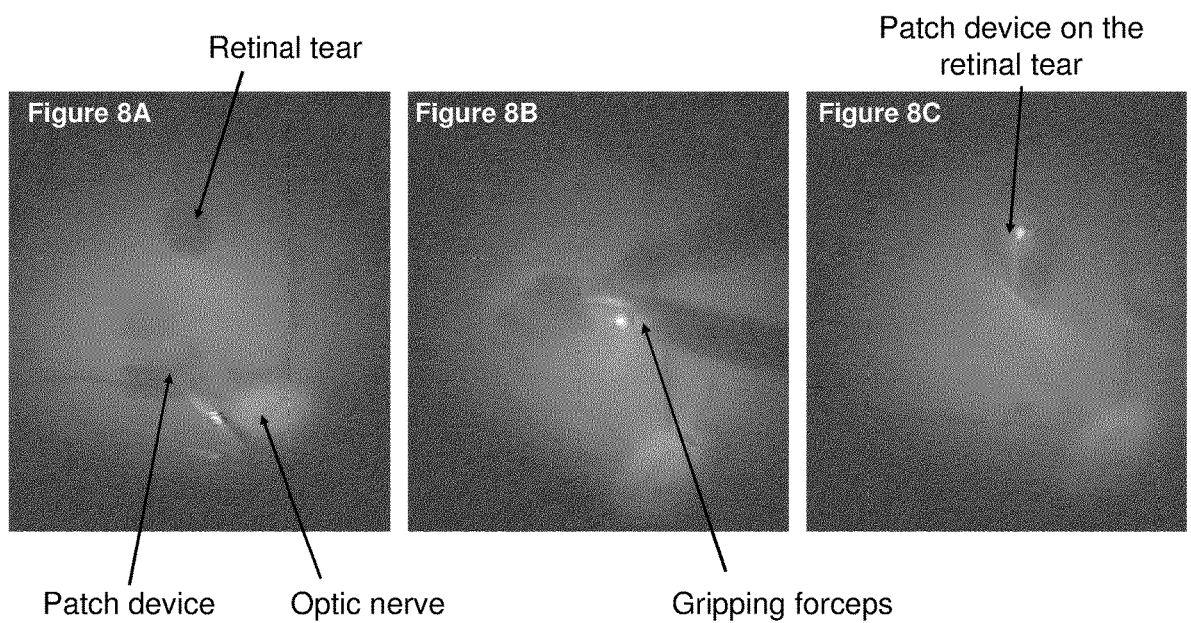
Snapshot images of placement of the patch device attached to retina in a rabbit eye

POLYMER SUBSTRATE RETINAL PATCH COATED WITH ADHESIVES

RELATED CASES

This application claims the benefit of U.S. Provisional Application No. 62/135,392, filed Mar. 19, 2015. This application and any other applications listed in the accompanying Application Data Sheet are incorporated in their entireties by reference herein.

FEDERAL FUNDING

Certain embodiments of the inventions disclosed herein were funded, at least in part, by National Science Foundation Grant No. NSF ERC EEC-0310723. The Federal Government may have certain rights in various embodiments of the inventions disclosed herein.

BACKGROUND

Field

Several embodiments relate generally to adhesible substrates suitable for implantation into the eye. In several embodiments, such substrates are either chemically and/or biologically adhesive and are useful for the permanent or temporary closure of ocular tears and ruptures, and reattachment of the retina to the posterior wall of the eye.

Description of the Related Art

Detachment of the retina from the underlying sub-retinal tissue is an injury that can lead to partial or complete blindness if not repaired. Current repair methods involve pneumatic or laser mechanisms to promote retinal reattachment. Retinal detachment remains a major cause of vision loss worldwide. The frequency of retinal detachment in individuals with normal eyes varies from country to country, ranging from 6.3 to 17.9 per 100,000 population members, with a rate of approximately 12 per 100,000 in the United States. Detachment is more frequent with advanced age as well as in those individuals with severe myopia, those that have had cataract surgery or those with diabetic retinopathy.

SUMMARY

Provided in several embodiments is a patch configured to repair damaged ocular tissue, comprising a polymer matrix comprising a polymer, such as parylene (e.g., parylene-C), and having a first and a second substantially planar surfaces and a first adhesive component. In some embodiments, the first adhesive component comprises a plurality of disintegrins coupled with at least a portion of the surface area the first planar face of the patch. In some embodiments, the disintegrins (or other adhesive) cover the entire face of the patch. In several embodiments, the patch with the adhesive are configured for surgical implantation into the eye of a subject having retinal damage, such as for example, a retinal tear, hole, dialyses, detachment or other type of damage. In several embodiments, the positioning of the patch over or adjacent to the retinal damage is performed by surgically accessing the eye and placing the first adhesive coupled face of the parylene path in contact with the retina in a damaged region, which allows the patch to stabilize the retinal damage and initiates repair of the damaged ocular tissue. In several embodiments, the disintegrin comprises vicrostatin, contortrostatin, ADAM derived polypeptides, or combinations thereof.

In several embodiments, the retinal damage comprises retinal detachment (partial or complete) and the patch further comprises a second adhesive component (e.g., at least a portion of the second planar face of the patch) wherein the patch is configured for implantation into the subretinal space to reattach the retina to the choroid. The patch is "sandwiched" between the detached retina and the choroid, and the adhesives allow the patch to function as a stabilizing bridge to reattach the retina. In several embodiments, the patch bioerodes over time, which allows the retina to naturally reattach to the choroid. In several embodiments, the second adhesive component comprises a disintegrin, fibronectin, laminin, collagen, vitronectin or elastin, or combinations of these.

In several embodiments, the plurality of disintegrins exhibit high affinity for integrin subunits such as $\alpha$IIb, $\alpha$v, $\alpha$5, $\beta$1, $\beta$3 and $\beta$5. In several embodiments, the patch is annular, fenestrated, or otherwise configured to facilitate oxygen and nutrient passage through the patch.

In additional embodiments, the patch is generated in the absence of a specific substrate structure, and rather is comprised of one or more adhesives that are applied to the retina in order to lend stability to the damaged region. For example, an adhesive that polymerizes in situ can be applied to the retinal tear, which supports the damaged tissue. Additionally, in several embodiments that comprise a separate patch substrate, the one or more adhesives can be applied prior to implantation, or in alternative embodiments, after implantation.

In several embodiments, there is also provided a biocompatible patch, comprising a polymer matrix, a first adhesive component and optionally, a second adhesive component, the patch and adhesive being configured for surgical implantation, for example into ocular tissue. In several embodiments, the patch and adhesive are configured for surgical implantation on ocular tissues, to adhere to ocular tears/breaks, or to reattach the retina to the posterior wall of the eye.

In several embodiments, the patch comprises a polymer or polymer blend. In some such embodiments, the polymer is selected from the group of polyimide, silicone, parylene, and combinations thereof. In some embodiments, the polymer comprises parylene-C.

In several embodiments, the polymer (or polymer blend) is a bio-erodible polymer selected from the group consisting of poly(caprolactone), poly(lactic acid), poly(glycolic acid), polyglactin, poly(lactic-co-glycolic acid), starch, collagen, and combinations thereof.

In some embodiments, the patch comprises two adhesive components (or more than two). Depending on the embodiment, the first and second adhesive components can be the same, or alternatively can be different. Ratios or blends of two or more adhesives can also be used, in several embodiments.

In several embodiments, the adhesive component(s) are optionally reversibly adhesive. For example, in several embodiments, the adhesive component(s) comprise a reverse thermal polymer. In some such embodiments, the reverse thermal polymer comprises pNIPAM. In additional embodiments, the adhesive is reversible by way of a solvent or other material that reduces the ability of the adhesive to maintain its adherence between the patch and ocular tissue. In several embodiments, the first adhesive component, the second adhesive component, or both the first and second adhesive components comprise a disintegrin. Fibronectin, laminin, collagen, vitronectin or elastin. In some embodiments, the first and/or second adhesive component comprises disintegrin, vicrostatin, contortrostatin, or ADAM derived polypeptides. In addition, in several embodiments, the reversion of the adhesive to a non-adherent state is by cleaving the by one or more enzymes, wherein the one or more enzymes are selected from the group consisting of elastase, urokinase, plasmin and tissue plasminogen activator.

In several embodiments, depending on the treatment to be rendered, the patch can be configured for temporary attachment or optionally for permanent attachment. In several embodiments, the patch is used for treating ocular tissue such as the cornea, sclera, lens or retina.

In several embodiments, there are also provided methods of treating a damaged or diseased ocular tissue, such as the retina. In one embodiment, there is provide a method for the reattachment of a detached retina of a subject comprising surgically accessing the vitreous cavity of the eye of the subject and implanting onto the surface of a detached portion of the subject's retina one or more biocompatible patches, the patches comprising a polymer matrix and at least a first adhesive component and optionally, a second adhesive component, wherein the patch or patches function to adhere the detached portion of the retina to the sub-retinal tissue.

Disclosed herein are methods and compositions for treating ocular injuries or retinal detachment by adhering one or more polymer patches to the affected site to facilitate healing. In some embodiments, the patch comprises a polymer matrix or sheet, and either one or two adhesive components attached to the surfaces of the sheet. In several embodiments, three or more adhesive components can be used. The patch is configured for surgical implantation, in several embodiments, especially for implantation into the eye. In several embodiments, the "patch" is comprised of a polymeric composition that polymerizes upon administration to an ocular tissue in need of repair. In several embodiments, such a composition is made up of two or more components that react with one another (and/or ocular tissue/fluid) to polymerize or assemble into a stabilizing patch. The surgical implantation may be within the tissues of the eye, to repair ocular tears or breaks or to reattach the retina to the posterior wall of the eye, especially in cases of retinal injury, retinal tears, retinal holes dialyses, or retinal detachment. The patch may be placed, in accordance with the methods described herein, over or adjacent to the site of retinal damage, on either the vitreous-facing or choroid-facing surfaces of the retina. The patch may also be placed in the subretinal space such that it adheres to both the retinal surface and the choroid, attaching the retina to the choroid. In some embodiments the polymer comprises polyimide, silicone or parylene, including parylene-C. The patch may also comprise a bio-erodable polymer and may comprise poly(caprolactone), poly(lactic acid), poly(glycolic acid), polyglactin, poly(lactic-co-glycolic acid), starch or collagen. The adhesive components applied to the patch may be the same, or different, and each adhesive component may comprise more than one type of adhesive molecule. The adhesive may be a reverse thermal polymer, such as pNIPAM. The adhesive may also be a biomolecule, such as a disintegrin (such as vicrostatin, contortrostatin, and ADAM-derived peptides, or other natural or engineered disintegrins showing high affinity for integrin subunits $\alpha$IIb, $\alpha$v, $\alpha$5, $\beta$1, $\beta$3 or $\beta$5), fibronectin, laminin, collagen, vitronectin, or elastin. In some embodiments, the adhesive can be cleaved by enzymes, such as elastase, urokinase, plasmin, or tissue plasminogen activator, to facilitate removal of the patch. The patch may be configured for either temporary or permanent attachment, and may be attached to the cornea, sclera, lens, retina, or other ocular tissues. The patch may be fenestrated to allow oxygen and nutrient passage through the patch to the site of injury, or it may be otherwise custom-configured to fit the site of the injury. The patch may also be generated at the site of injury by injection of self-assembling polymer-adhesive conjugates.

Also provided herein are embodiments of methods of reattaching a detached retina or of facilitating the healing of an ocular injury by implanting (e.g. surgically) one or more of the patches described herein such that the patch adheres the detached portion of the retina to the sub-retinal tissue, or covers the site of injury to promote healing.

BRIEF DESCRIPTION OF THE DRAWINGS

FIG. 1A shows a simplified cross sectional diagram of patch 10 with an adhesive coating 20. FIG. 1B depicts a patch 10 having two regions of adhesive 20*a* and 20*b*. In accordance with several embodiments, adhesive 20*a* and 20*b* may be the same or may be different adhesives, depending on the embodiment. FIG. 1C depicts a patch according to several embodiments disclosed herein, including two regions of adhesive, placed on opposing faces of the patch. According to several embodiments, adhesive 20*a* and 20*b* may be the same or may be different adhesives, depending on the embodiment.

FIGS. 2A-2C shows a simple cross sectional diagram of various patch positions with respect to ocular tissue according to several embodiments disclosed herein. FIG. 2A shows an example of the application of a patch 10 with a one-sided coating of adhesive 20 to the surface of an ocular tissue 30 to effect or support closure or support of a damaged ocular tissue 40 (e.g., a tear or hole such as in the case of a retinal tear or hole, corneal laceration, detachment, scleral laceration or anterior or posterior lens capsule ruptures, etc.). FIG. 2B shows an example of the application of a patch 10 with a patterned one-sided coating of adhesive (20), which can be affixed on the margins of a detached ocular tissue (40), such as the retina, in such a manner as to push the detached portion of the retina into conformity with the back of the eye. FIG. 2C shows an example of the application of a patch 10 with a two-sided adhesive coating (20*a/b*) which can be placed between ocular tissue 30 and another ocular tissue layer (50) to promote adhesion between the layers such as, for example, in the subretinal space to attach different retinal layers together and close a retinal rupture or tear, between the sclera and conjunctiva for scleral tear closure, or between the corneal lenticle and the preserved cornea.

FIGS. 4A-4C show schematic sketches of a cross section of an eye with either a rhegmatogenous or an atrophic retinal tear. FIG. 4A shows a cross sectional sketch showing the wall of an eye with the patch 10 placed on the surface of a retina having a rhegmatogenous tear or hole 40. FIG. 4B depicts sub-retinal placement of the patch 10 such as a patch placed between the wall of an eye and a retina 30 having an atrophic retinal rupture or tear. In an atrophic retinal rupture there is generally no tissue portion covering the opening in the retina. FIG. 4C shows a close-up of one contemplated placement of the patch 10 according to several embodiments herein, wherein, in an atrophic retinal rupture, a patch 10 that is coated on both sides with adhesive 20 can be used to adhere remaining retinal 30 tissue to the choroid 60.

FIGS. 8A-8C depict experimental placement of patches on retinal damage according to several embodiments disclosed herein. FIG. 8A is a photograph of a retinal tear in a rabbit eye. FIG. 8B is a photograph depicting experimental placement of a retinal patch 10 on a retinal tear 40 in a rabbit eye by using a gripping forceps. FIG. 8C is a photograph of an experiment depicting implantation of a retinal patch 10 attached to the retina in accordance with several embodiments disclosed herein.

DETAILED DESCRIPTION

Figure 1A:
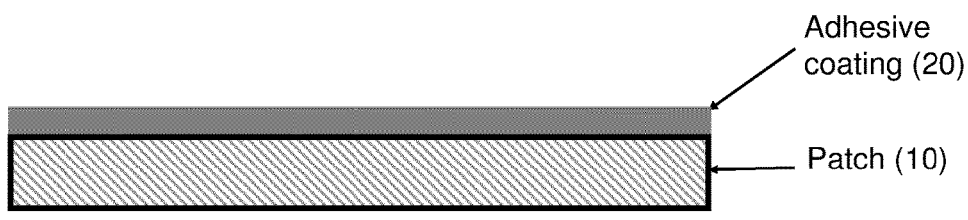
FIGS. 1A-1C depict schematics of patches according to several embodiments herein.

Examples of conditions leading to retinal damage include retinal tears, retinal detachment, macular holes, penetrating eye injuries, and posterior capsule rupture, though any injury leading to separation of the retina or damage to the retina, macula, choroid, or other ocular tissues may be treated using the compositions and methods described herein. Retinal tears or retinal breaks arise from excessive traction or pressure on the retinal layers, which most frequently occurs in patients who suffer from trauma, high myopia, or certain inflammatory or infectious conditions of the eye. As the retina tears, one or more retinal blood vessels may also be torn or damaged, causing vitreous hemorrhage, possibly producing "floaters" (specks or cobweb-like shadows within the field of vision). Further, when the fluid in the eyes leaks through the retinal tear, it causes retinal detachment.

A macular hole is a small break in the macula, which is essentially the center of the retina. When the vitreous humor loses its jellylike consistency and liquefies, which happens most in older individuals, the retina can be pulled away from the retina to cause a hole. The causative factors for this kind of shrinkage of the vitreous humor include inflammatory cystoid macular edema and vascular disorders of the retina.

Penetrating eye injuries such as corneal/scleral laceration, usually caused by foreign bodies or significant force striking the eye, result in a tear partially or fully through the cornea/sclera. A full thickness laceration will cut completely through the cornea/sclera and cause a ruptured globe. Current treatment is to close the eye wall using sutures. The suturing surgery causes discomfort, and will subsequently lead to eye-rubbing, which can lead to inflammation and complications in healing.

Posterior lens capsule (PC) rupture is a common intraoperative complication of cataract surgery and may be associated with a poor visual outcome owing to cystoid macular edema and retinal detachment. Tears of the anterior capsule, although relatively rare, may occur during capsulorrhexis, lens sculpting, and removal of nuclear fragments. A significant risk of an anterior capsular tear is that it can wrap around the equator and extend into the posterior capsule, increasing the risk for a subsequently dropped nucleus. When a posterior capsular tear occurs in cataract surgery, an ophthalmic viscosurgical device (OVD) can be placed in the anterior chamber to flatten the anterior capsule, thus reducing stress on the capsule. Although injecting an OVD into the anterior chamber helps to maintain anterior chamber stability and tamponade the tear, the lens capsule might still not able to support a lens due to the defect. The problem of stabilizing the lens in the capsule with high efficiency is currently clinically unsolved.

There are an estimated 1.2 million open wound or contusion eye injuries in the U.S. each year, and injury is the most common cause of monocular blindness. An ocular patch readily available to ophthalmologists could have a significant impact with respect to retaining vision following a traumatic injury.

Thus, there is a need for methods and compositions for treating ocular tear/hole, rupture, and retinal detachment.

Retinopexy (retinal detachment) is currently treated using scleral buckling, gas (pneumatic) or oil bubbles, laser treatments, or cryotherapy. Disadvantages of scleral buckling include frequent induction of postoperative myopia, difficulty in management of very large and/or posterior retinal breaks and the rare possibilities of buckle erosion or induced strabismus. In pneumatic retinopexy, fluid (gas or oil) of significantly higher or lower density (vs. water) is used to apply a distributed force to press the detached retina against the choroid to promote reattachment. Because detached retinas occur in the posterior (rear) portion of the eye, this requires the patient to either lay in a supine or prone position to allow the bubble to "float" or oil droplet to "sink". This position must be held for several hours to ensure good reattachment. The gas/oil is eventually metabolized. Pneumatic retinopexy has the additional disadvantage of stringent requirements for appropriate patient selection. In laser retinopexy, a laser is used to burn or stitch the retina to the choroid. However, patient discomfort and some collateral vision loss may occur. Other alternative techniques to maintain the retina in a sealed state after a surgical procedure are either unstable or their chemical characteristics can damage the retinal tissues and the contiguous eye structures, both in short term and long term.

Effectively sealing a breakage in the retinal surface is a significant challenge in retinopexy surgery. A proper seal on the retina can provide a successful and lasting positive surgical outcome. Improper sealing can result in re-detachment, retinal hypoxia and subsequent permanent vision loss. To address the shortcomings of current treatments for retinal detachment, several embodiments of the invention provided herein are directed to polymeric retinal patches that are configured to permanently or temporarily reattach the retina. Polymers such as silicone, polyimide and parylene have been proven to be compatible and non immuno-reactive to eye tissues. The polymers are treated on their opposing sides (e.g., the front and back, or anterior and posterior) in order to render them adhesive. Adhesion is accomplished either via chemistry (e.g., additional polymers) or biologically (e.g., proteins that will interact with resident ocular proteins). In several embodiments, the polymeric patches disclosed herein improve the comfort and effectiveness of retinal reattachment.

Polymers

Provided herein is a patch 10 that in some embodiments comprises a polymer, wherein the surface of the substrate is coated with one or more adhesives. In several embodiments, however, administration of certain adhesive compositions allow the generation of an "patch" without the additional use of a separate polymeric substrate or material, in that the adhesive compositions react one with one another and coalesce to form a sheet that functions to repair or amend damage to the retinal tissue. Nonlimiting examples of polymer patches include polymer sheets, films, fiber matrices, coatings, and hydrogels. In several embodiments, adhesive(s) is/are able to form polymer patch(es) without any additive. In several embodiments, polymers that are biocompatible with ocular tissues are used to construct the retinal adhesive patches disclosed herein. In several embodiments, the polymers are bio-inert. In still additional embodiments the polymers are and non-immuno-reactive. In several embodiments, homopolymers, polymer blends and copolymers, such as random copolymers and block copolymers are used. In several embodiments, the polymeric material comprises ethylvinyl acetate-polyethylene, elastane, parylene (including but not limited to parylene A, C, M, and other treated parylenes), polyimide, polyurethane, silk fibroin, polypropylene, nylon and/or polyamide are used. Combinations of these polymers may also be used. In some embodiments, the polymeric material comprises copolymers or block copolymers, thermoplastic polyurethanes silicone-modified polyether urethanes, poly(carbonate urethane). In some embodiments, the polymeric material may also comprise thermoplastic polyurethanes, polymers or copolymers which may comprise aliphatic polyurethanes, aromatic polyurethanes, polyurethane hydrogel-forming materials, hydrophilic polyurethanes, or combinations thereof. In some embodiments, the patch has a thickness in a range of about 5 µm to about 50 µm. In some embodiments, the patch has a thickness in a range of 5 nm to 50 µm. In some embodiments, the patch has a thickness in a range of 5 nm to 40 µm. In some embodiments, the patch has a thickness in a range of 5 nm to 30 µm. In some embodiments, the patch has a thickness in a range of 5 nm to 20 µm. In some embodiments, the patch has a thickness in a range of 5 nm to 20 µm. In some embodiments, the patch has a thickness in a range of 5 nm to 1 µm. In some embodiments, the patch has a thickness in a range of 50 nm to 1 µm. In some embodiments, the patch has a thickness in a range of 100 nm to 800 nm. In some other embodiments, patches have a thickness in a range of from about 5 nm to about 500 µm. In some other embodiments, patches have a thickness in a range of from 5 nm to 400 µm. In some other embodiments, patches have a thickness in a range of from 5 nm to 300 µm. In some other embodiments, patches have a thickness in a range of from 5 nm to 300 µm. In some other embodiments, patches have a thickness in a range of from 5 nm to 100 µm. In some other embodiments, patches have a thickness in a range of from 5 nm to 50 µm. In some other embodiments, patches have a thickness in a range of from 5 nm to 5 µm. In some other embodiments, patches have a thickness in a range of from 5 nm to 1 µm. In some other embodiments, patches have a thickness in a range of from 50 nm to 1 µm. In some other embodiments, patches have a thickness in a range of from 100 nm to 1 µm. In some other embodiments, patches have a thickness in a range of from 100 nm to 800 µm. Any thicknesses between those listed can also be used, in certain embodiments, depending on the material the patch is made of. For example, in several embodiments in which the patch comprises parylene, the patch has a thickness in a range of about 5 nm to about 100 nm, about 100 nm to about 500 nm, about 500 nm to about 1 µm, about 1 µm to about 5 µm, about 5 µm to about 10 µm, about 10 µm to about 20 µm, about 20 to about 30 µm, about 30 to about 40 µm, about 40 to about 50 µm, about 50 to about 100 µm, etc. (including thicknesses between those listed). In some embodiments the patch has a tensile modulus of about 10 KPa to about 100 MPa. In some further embodiments the polymeric patch is designed as low a tensile modulus as possible to reduce the mechanical mismatch between the patch and ocular tissues. In several embodiments, tensile modulus is customized, depending on the location the patch is to be applied.

In several embodiments, the polymeric material may comprise one or more erodible polymers, such as poly (caprolactone), poly(lactic acid), poly(glycolic acid), polyglactin, poly(lactic-co-glycolic acid), polyethylene-vinyl acetate, poly(D,L-lactic acid), poly(glycolic acid-co-trimethylene carbonate), poly(amino acids), poly(glycolide-co-caprolactone), poly(hydroxybutyrate-co-valerate), polydioxanone, poly(trimethylene carbonate), poliglecaprone, poly(iminocarbonate), copoly(ether-esters), polyalkylene oxalates, polyphosphazenes, poly depsi-peptide carbonate, polyethylene-oxide based polyesters, poly-N-alkylacrylamides, hyaluronic acid, fibrin, fibrinogen, cellulose, starch, collagen, heparinized collagen, vitronectin, laminin, and combinations thereof. Advantageously, in certain embodiments less than 100% of the patch can be engineered to be bioerodible. For example certain types of retinal damage or tears may benefit from treatment with a patch in which a portion of the patch erodes over time. In such embodiments the materials used to generate the patch can be blended and/or constructed in modular segments in order to allow a portion of the patch to be positioned in an area where bio erosion is desirable, where is another portion of the patch is positioned in an adjacent position (or even a distant position) where in that portion of the patch is permanent (at least until optionally removed by a surgical procedure). In some embodiments, the polymeric material may comprise decellularized tissue. In some further embodiments, the polymeric matrix may comprise decellularized ocular tissue. In other embodiments, the polymeric matrix may comprise isolated extracellular matrix. In other embodiments, the polymeric material may comprise a chitosan fiber or film, or a microcrystalline cellulose fiber or film.

In additional embodiments, the polymeric material may comprise other polymers, such as silicone elastomer based on vinyl, phenyl, and methyl gums (including, for example, vinyl-functional poly(dimethylsiloxanes), poly(aryl)/(poly phenyl)siloxanes, and poly(dimethyl-diphenyl)siloxanes. In some embodiments, a silicone based polymeric patch has a thickness in a range of from about 50 nm to about 3 mm. In some embodiments, a silicone based polymeric patch has a thickness in a range of from 50 nm to 3 mm. In some embodiments, a silicone based polymeric patch has a thickness in a range of from 50 nm to 1 mm. In some embodiments, a silicone based polymeric patch has a thickness in a range of from 50 nm to 500 µm. In some embodiments, a silicone based polymeric patch has a thickness in a range of from 50 nm to 100 µm. In some embodiments, a silicone based polymeric patch has a thickness in a range of from 50 nm to 1 µm. In some embodiments, a silicone based polymeric patch has a thickness in a range of from 100 nm to 1 µm. In some embodiments, a silicone based polymeric patch has a thickness in a range of from 500 nm to 1 µm.

In still additional embodiments combinations of various polymers can be used to achieve a patch with certain desirable characteristics. For example, depending on the type of damage to retinal tissue, or the desired site of implantation within a subretinal space or other ocular environment, it may be desirable to generate a patch with one or more thick regions and one or more thin regions. This may be the case for example when a portion of the retina has been substantially lifted off of the choroid in one region (where a thicker patch may be desirable) wears and another region there is a smaller distance between the retina and the choroid (in which case a somewhat thinner portion of the patch may be desirable) additionally differences in characteristics such as flexibility, durability, tensile strength, solubility, ability to be manipulated (e.g. by the insertion instruments) or other characteristics can be tailored for a particular patch or for implantation into a particular patient.

Adhesives

In several embodiments, the polymeric patch is treated with adhesives that are reversible or irreversible and may comprise small molecule adhesives, polymers, biopolymers, polysaccharides, polypeptides, and any combination thereof. In several embodiments, the patch is treated, coated, or otherwise coupled with polymeric adhesive. In several embodiments, the adhesive may be pre-activated (e.g., is already sticky), while in others, contact with ocular fluid activates the adhesive. Additional embodiments involve activation of the adhesive by an external stimulus (e.g., after placement of patch). Examples of external stimuli include, but are not limited to heat, ultrasound, radio frequency, light or laser energy, or microwaves. In several embodiments, reverse thermal polymers are used (e.g., those that are sticky/adhesive at body temperature, but not at room temperature). In several embodiments, pNIPAM (a reverse thermal adhesive; poly(N-isopropylacrylamide, also known as PNIPA, PNIPAAm, NIPA, PNIPAA or PNIPAm) is used to adhere the patch to the retina and/or the underlying tissue. pNIPAM transitions between hydrophobic and hydrophilic states with changes in temperature. These changes in hydrophobicity/hydrophilicity correlate with adhesive/non-adhesive characteristics and thus, in several embodiments, allow adhesion of the patches to ocular tissues when implanted and exposed to body temperature. Moreover, in several embodiments, site-directed cooling of the patch (e.g., by water-pick or air) can be used to cause the pNIPAM to lose adherence and thus enable removal (or repositioning) of the patch. In one or more embodiments, the pNIPAM can be deposited via one of two processes: either a wet chemical synthesis called atom transfer radical polymerization (ATRP) or via a chemical vapor deposition (CVD) process. The ATRP approach produces thin pNIPAM layer (<100 nm thickness). The CVD approach enables thicker deposits (e.g. 100 nm to 1,000 nm) of pNIPAM. Other deposition techniques may be used, in additional embodiments.

Biological adhesives such as adhesives utilizing peptides, proteins, amino acids, nucleotides, polynucleotides, nucleic acids, saccharides, polysaccharides, phospholipids, lipopolysaccharides, lipoproteins, fatty acids, mono- di- or triglycerides, or any molecule with adherent properties that is or could be derived from biological tissue, are also used in several embodiments. Combinations of these agents may also be used. For example, integrins function as receptors that interact with the elements from the extracellular matrix (ECM), connecting the cytoskeleton with the cell surface. Their structure is heterodimeric, composed of alpha and beta chains, which are expressed in the surface of the mammalian cells. Extracellular matrix (ECM) proteins can be used to bind integrins via tripeptide Arg-Gly-Asp (RGD)-containing segments at the cellular interface. Nonlimiting examples include fibronectin, laminin, and collagen, vitronectin and elastin. Non-ECM proteins that contain one or more RGD segments are another example of compounds capable of binding to integrins; specific examples are disintegrins. Disintegrins are small, disulfide-rich, RGD-containing peptides that bind with high affinity to integrin subunits such as $\alpha IIb$, $\alpha v$, $\alpha 5$, $\beta 1$, $\beta 3$ and $\beta 5$. Thus, the molecular interaction between integrins and disintegrins is used in several embodiments to adhere the detached retina back to the underlying tissue via the patch. In several embodiments, the integrins and/or disintegrins are naturally occurring, while in several embodiments they are engineered. For example, in several embodiments, vicrostatin (a chimeric disintegrin generated recombinantly by grafting the C-terminal tail of the viperid snake venom disintegrin echistatin to the sequence of the crotalid disintegrin contortrostatin) is used to coat one or more surfaces of the patch. In other embodiments, the disintegrins comprise ADAM (A Disintegrin and Metalloproteinase) derived polypeptides. Other disintegrins and/or integrins are used, depending on the embodiments. Moreover, in several embodiments, other molecular or immune interactions are used (e.g., antigen-antibody, ligand-receptor, etc.). In several embodiments, the biological adhesives are preferred. In several embodiments, site-directed enzymatic digestion can disrupt the adherence, should the patch need to be removed or repositioned. Herein, the enzymes that used to cleave the adherence contains, but are not limited to, trypsin, pepsin, collagenase, elastase, urokinase, plasmin and tissue plasminogen activator (tPA).

In some embodiments, the patch self-assembles in situ based on the cohesive properties of an injected adhesive. Such an adhesive may comprise disintegrins or disintegrin conjugates, or other adhesives known in the art such as methacrylate adhesives or polymers; copolymers; polysaccharides; proteins; or combinations thereof. As discussed above, such a self-assembling patch does not require an additional polymeric (or other material) substrate onto which the adhesive molecules are deposited. Rather, an activator component, or two components that react with one another, can be applied to the site of treatment and function (as a result of the structure that results from the activation of the materials) as a patch that repairs or mends damaged retinal tissue. In some embodiments, the adhesive comprises a collagen molecule and/or a collagen binding protein. In some embodiments, the adhesive comprises a fusion between an integrin, disintegrin or other adhesive and another protein that is capable of self-assembly. In some embodiments, the self-assembling protein is collagen or a collagen binding protein. In some further embodiments, the adhesive comprises a fusion between an integrin, disintegrin or other adhesive and a nucleic acid. In some further embodiments, the nucleic acid is capable of self assembly. In still further embodiments, the nucleic acid comprises RNA, DNA, peptide-nucleic acid, or any combination or subcombination thereof. In some embodiments the adhesive comprises a fusion between integrin, disintegrin or other adhesive and a fatty acid, glycolipid, phospholipid, mono-di- or triglyceride, and/or sterol. In some embodiments, an integrin, disintegrin or other adhesive is covalently or noncovalently attached to a polymer, copolymer, or a monomer component thereof. In some embodiments, a single integrin, disintegrin, or chemical adhesive is attached to a polymer. In some further embodiments, multiple integrin, disintegrin, or chemical adhesive moieties are attached to a single polymer molecule. In several embodiments, layers of adhesives may be used, or different patterns can be used in order to ensure appropriate attachment to the tissue to be treated. Additionally, depending on the embodiment, different adhesives (either within a class or in different classes) can readily be used in different regions or layers on the patch. In some further embodiments, the polymer is a linear polymer. In some further embodiments, the polymer is a branched polymer. In some embodiments the patch is formed by injecting a composition comprising a monomer, a monomer attached to an integrin, disintegrin, or adhesive, a crosslinker, and/or a catalyst into the subretinal space, wherein the patch will form by polymerization in situ. Such polymerization may be brought about by chemical catalysts, photopolymerization, thermal polymerization, or by any method known in the art to carry out a polymerization process.

In some embodiments the adhesive comprises of a cell-penetrating peptide, antimicrobial peptide, cytolytic peptide, or pore-forming peptide, including an isolated or synthetic transmembrane domain.

By way of non-limiting example, in one embodiment, to attach the adhesive to the polymer, a monochromatic excimer laser allows for the "activation" of the polymer substrate. Activation by an intense ultraviolet light source (e.g., an excimer laser) under a specific wavelength, power and pulse rate, irradiates the surface or surfaces needed of the polymer to break chemical bonds and form unpaired electrons from the polymer substrate. After laser processing of the polymers, solutions containing, for example, vicrostatin (VCN) are applied to the polymer for a period of time (e.g., minutes to hours). As result, covalent bonding of the peptides to the polymers are generated.

Figure 1B:
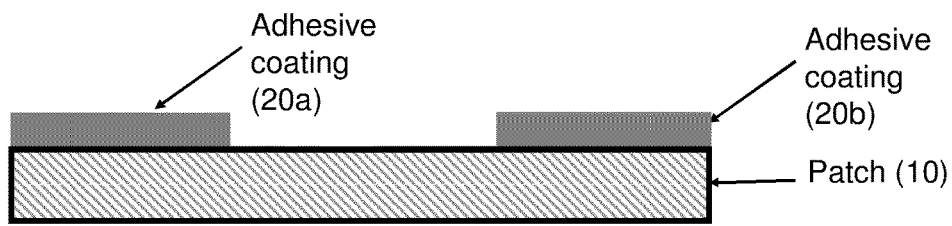
Figure 1C:
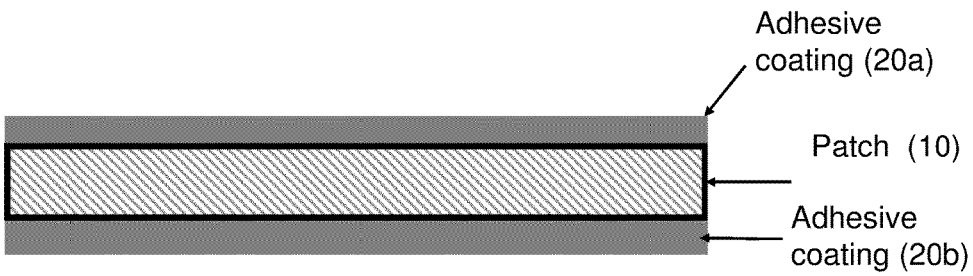

The adhesive composition is optionally different on the two sides of the patch. See, for example, FIG. 1C. For example, in several embodiments, the patch is coated with a chemical adhesive on a first side and a biological adhesive on the second side. In some embodiments, however, the same type of adhesive is used on both sides. However, in still additional embodiments, different specific adhesive compounds, though of the same type, are used on opposing sides of the implant (e.g., a first chemical adhesive on the first side and a second chemical adhesive on the second side). Mixtures of chemical and biological adhesives on a single side are also used, depending on the embodiment. In some embodiments, only a single side of the patch is coated with an adhesive, while in other embodiments, the placement of adhesive is customized to suit the shape of the injury (see FIG. 1B and FIG. 2B, for example). As discussed above various patient-specific applications of adhesive material can be employed in certain embodiments, these allow for the structure of the patch that is ultimately implanted to be tailored to the ocular anatomy of that patient, and the severity or location of the damage to the ocular tissue. In still additional embodiments however the patch need not be fully customized prior to implantation, but rather can be implanted and adhesive can be used to supplement the overall size and shape of the patch according to the specifics of a given patient needs.

Customization

Various types of retinal detachment can occur. For example, a rhegmatogenous retinal detachment occurs due to a break in the retina (also called a retinal tear). That tear allows fluid to pass from the vitreous space into the subretinal space (thus forcing fluid in between the between the sensory retina and the supportive retinal pigment epithelium). These tear can manifest as holes, tears (e.g., a longitudinal split or rip) and dialyses. Holes form due to retinal atrophy especially within an area of lattice degeneration. Tears are due to vitreoretinal traction. Dialyses which are very peripheral and circumferential may be either tractional or atrophic, the atrophic form most often occurring as idiopathic dialyses in younger patients.

Another form of detachment is exudative detachment (a secondary retinal detachment). These occur due to inflammation, injury or vascular abnormalities and result in fluid accumulating underneath the retina without the presence of a hole, tear, or break.

Traction retinal detachment occurs when fibrous or fibrovascular tissue (which may be caused by injury, inflammation or neovascularization) exerts a non-normal force on the retina and causes the retina to pull away from the underlying retinal pigment epithelium.

Because of the variety of types of detachment, several embodiments of the patch disclosed herein are customizable. In several embodiments, the patches are shaped and adapted to the eye dimensions and tissues thickness of a specific patient and based on that patient's ocular anatomy, the type of detachment, etc. In several embodiments, an initial diagnosis and assessment is made, for example by retinal imaging or ultrasound, and the patch is customized to the type, size and degree of retinal damage. Thus, depending on the embodiment, the patch may be circular, oblong, square, rectangular, triangular, polygonal, or free-form (e.g., cut to fit). In those embodiments wherein a plurality of patches are used, combinations of shapes may be employed, depending on the location and/or type of detachment.

Moreover, because the retina receives ~50% of its nutrient supply from the choroid vasculature, in several embodiments the patch (or patches) are made no larger than is necessary for repairing the detachment (thereby allowing the choroid to supply the remainder of the reattached retina with nutrients). To facilitate the reattachment and re-supply of the retina with nutrients, in several embodiments, the polymeric patch (or patches) are cut to specific shape (e.g., to match or approximate the dimensions of a hole or tear). In several embodiments, the patch is fenestrated or annular in shape, to as to facilitate blood and nutrient transfer. In several embodiments, the polymeric patch is dimensioned such that oxygen and/or nutrient transfer can occur through the patch. In several embodiments, the patch is permeable to oxygen and/or nutrients.

In several embodiments, one patch is used to reattach the retina. In several embodiments, a plurality of patches are used (e.g., to adhere specific regions of the detached retina while reducing and/or not impeding nutrient transfer). As discussed above, a plurality of patches (or a single custom manufactured patch) can be used to accommodate a particular patient's size, type or degree of retinal damage.

In some embodiments, the patch 10 is placed over the desired site (see FIGS. 2A and 4A). In further embodiments, the patch 10 is patterned such that adhesive is absent from a portion of the patch, so that the adhesive makes contact with the tissue surrounding the treatment site, without contacting the injury itself (see, for example, FIG. 2B). In some embodiments, the patch comprises adhesive (either different or the same, depending on the embodiment) on both sides and is emplaced between two tissue layers, thus adhering the layers together (See, for example, FIGS. 2C, 4B and 4C).

In some embodiments, the polymer patch incorporates an angiogenesis modulator, anti-inflammatory, antibiotic, or other medication. Exemplary angiogenesis modulators include but are not limited to, aflibercecpt, ranibizumab, and peganaptib. Exemplary anti-inflammatories include, but are not limited to, bromfenac, diclofenac, suprofen, flurbiprofen, ketorolac, cyclosporine, and nepafenac. Exemplary antibiotics or anti-infectives include, but are not limited to: tobramycin, sulfacetamide, ofloxacin, natamycin, moxifloxacin, levofloxacin, gentamycin, gatifloxacin, erythromycin, ciprofloxacin, besofloxacin, bacitracin, and azithromycin. Other drugs or agents may also be used, such as steroids, prostaglandins, antibodies, etc.

Surgical Implantation and Removal

As discussed above, the implantation of a patch according the embodiments disclosed herein may be permanent or temporary. Patches are also optionally, bio-erodible, biodegradable and/or soluble (e.g., in water or other solvent, such as ocular fluid). In several embodiments, surgical implantation is by routine vitrectomy. In several embodiments, a pars plana vitrectomy approach is used. In several embodiments, a 20G vitrectomy (or other size) is performed and then the temporal port is optionally extended. In several embodiments, the intraocular pressure is temporarily increased to maintain the eye stability. Then, in several embodiments, the retinal forceps are used to position the patch over the defect. In several embodiments, the patch is optionally rolled, folded, or otherwise configured to be introduced into the posterior chamber of the eye through a minimal access port. However, in other embodiments, a separate access port is generated to allow delivery of the patch without rolling or folding of the patch. The port is subsequently closed and the procedure is completed. Retrieving the patch, should removal (or repositioning) be desired, is accomplished in a similar manner. As discussed above, enzymatic disruption of biological adhesives is used in several embodiments to release the patch. Similarly, site-directed cooling is used in several embodiments to release those patches adhered with pNIPAM (or another reverse thermal adhesive). Other surgical implantation and removal approaches are also used, depending on the embodiments.

EXAMPLES

The description and examples provided herein are put forth to provide those of ordinary skill in the art with a complete disclosure and description of how the patches provided herein are made and evaluated, and are intended to be purely exemplary. It will be apparent to one of ordinary skill in the art that numerous modifications can be made without departing from the scope of the embodiments described herein.

Example 1

Preparation of Polymer Patches Coated with Adhesives

PNIPAM Treated Patch by Chemical Vapor Deposition:

Inside a vacuum chamber, acryloyl chloride monomer were flowed over parylene C substrates that were functionalized with vinyl groups on their surface. The rate of growth was controlled by the rate of flow of monomer and reactants. Following deposition, both patch types (the CVD and disintegrin, discussed below) were rinsed in de-ionized water to remove unpolymerized monomer. CVD-based patches were prepared using the conditions prescribed for growing pNIPAM thicknesses of 100 nm, 400 nm and 800 nm. To improve the network of pNIPAM chains in the substrate and improve anchoring, cross-linking groups may be added to the process.

Disintegrin Treated Patch:

Modification of defined areas of the silicone (Nusil MED-4860) and parylene C surface via laser processing was conducted in order to attach vicrostatin (VCN) to the surface of the patch. The silicone surface was irradiated with a monochromatic, intense ultraviolet excimer laser to form unpaired Si-dangling bond electrons. The silicone was then exposed to the VCN solution, incubated overnight to allow binding between the organic radicals upon the silicone and VCN, and washed in phosphate buffered saline. Different lasing parameters were investigated, and in this particular example, a laser wavelength of 248 nm, power of 10 KeV and pulse rate of 150 Hz were chosen as appropriate parameters to process the silicone and parylene C.

Example 2

Adhesion Evaluation

PNIPAM-treated parylene C and disintegrin-treated parylene C, synthesized using the approaches described in Example 1, were tested. Adhesion to dissected cadaveric porcine retinal tissue was characterized under ideal normal force conditions using a uniaxial tension tester.

The studies were conducted to assess whether the patches were capable of meeting the adhesion performance of retinal tissues in uniaxial tension testing. Additionally, the polymeric patches were assessed to determine whether the polymers as provided herein comprising the pNIPAM can be removed using a temperature lowering protocol, and whether the polymers as provided herein comprising disintegrin adhesives can be removed using an enzyme cleaving protocol utilizing an enzyme solution containing plasmin.

Results:

The attachment strengths between different individual patch and retina tissue are listed in Table 1, below. The pNIPAM treated parylene C sheet predictably and reversibly transitioned between high adhesive and low adhesive states in the desired temperatures. Attachment force was enhanced in proportion to the lased area on the polymer substrate, which was increased from 0 to 50%: about 2.8 orders of magnitude increase was seen in the pNIPAM-coated silicone sheet, and 2.4 order of magnitude increase was seen in the pNIPAM-coated parylene C sheet. Decreases in attachment strength were seen after treating the retina tissues with 20×BSS diluted plasmin (10 U/ml) solution.

TABLE 1

| Adhesive type | Polymer substrate | Thickness (nm) | Mean Maximum Adhesion Strength (mN) (n = 3) at 37.5° C. | Mean Maximum Adhesion Strength (mN) (n = 3) at 26° C. |
| --- | --- | --- | --- | --- |
| PNIPAM | Parylene C | 100 | 35.1 | 23.2 |
| PNIPAM | Parylene C | 400 | 46.9 | 20.2 |
| PNIPAM | Parylene C | 800 | 60.3 | 26.8 |

| Adhesive type | Polymer substrate | Lased area on substrate (%) | Mean Maximum Adhesion Strength (mN) (n = 3) | Mean Maximum Adhesion Strength (mN) (n = 3) treated with plasmin |
| --- | --- | --- | --- | --- |
| VCN | Parylene C | 0 | 32.5 | N/A |
| VCN | Parylene C | 25 | 55.8 | 31.6 |
| VCN | Parylene C | 50 | 78.2 | 26.7 |
| VCN | Silicone | 0 | 28.4 | N/A |
| VCN | Silicone | 25 | 36.5 | 38.4 |
| VCN | Silicone | 31 | 39.4 | 33.2 |
| VCN | Silicone | 37.5 | 47.5 | 37.3 |
| VCN | Silicone | 44 | 56.5 | 36.8 |
| VCN | Silicone | 50 | 79.2 | 33.5 |

Example 3

Evaluation of Retinal Patch in Cadaver Porcine Eyes

Experiments were performed to evaluate the use of disintegrins as adhesives to place and adhere a patch on the retinal surface of cadaveric porcine eye model, mimicking clinical cases. Integrins work as receptors that interact with the elements from the extracellular matrix (ECM), connecting the cytoskeleton with the cell surface. Their structure is heterodimeric, composed of alpha and beta chains, which are expressed in the surface of the mammalian cells. Disintegrins are small, disulfide-rich, RGD-containing peptides, which bind with high affinity to integrin subunits such as $\alpha IIb$, $\alpha v$, $\alpha \alpha 5$, $\alpha 1$, $\alpha 3$ and $\beta 5$.

Figure 3:
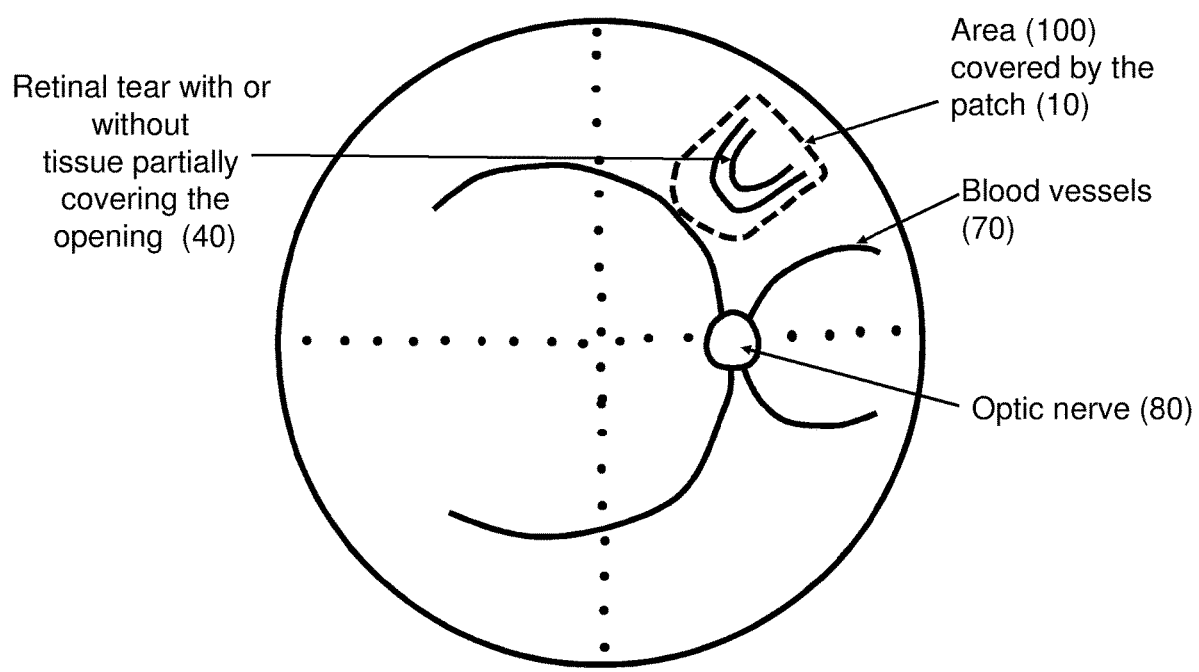
FIG. 3 shows a topological sketch of the posterior of an eye with a retinal tear 40, further showing an example of how a patch 10 would be placed to produce an area (100) covered by the patch in accordance with various embodiments disclosed herein. Shown for anatomic reference are blood vessels 70 and the optic nerve 100.
Figure 5:
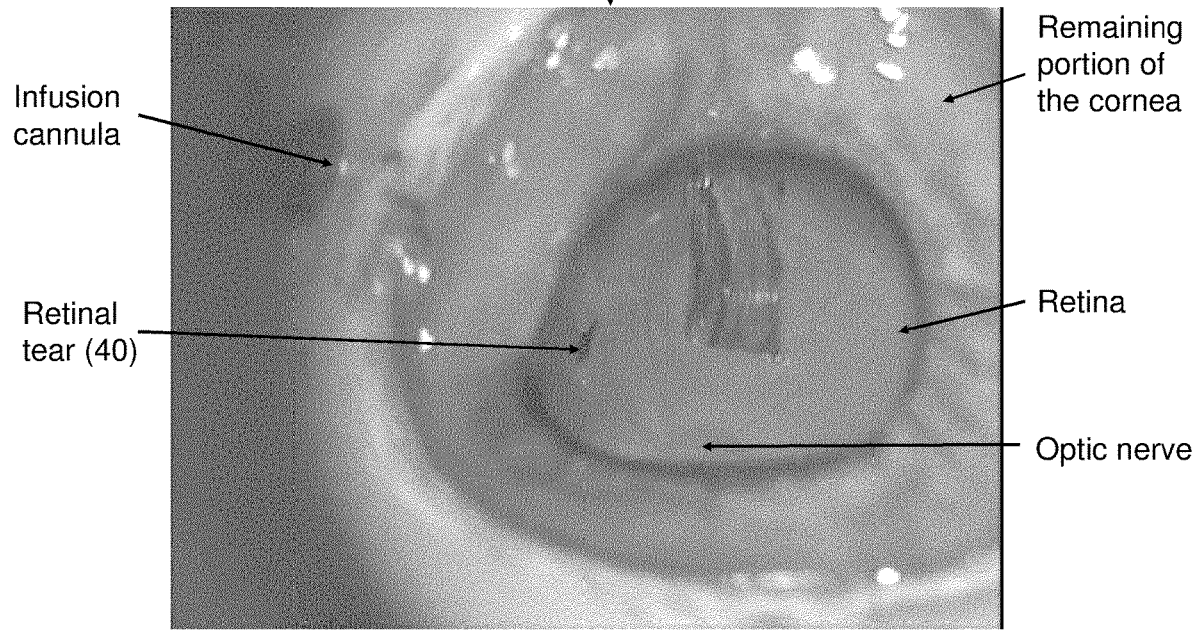
FIG. 5 is a photograph of a retinal tear in a cadaver porcine eye.
Figure 6:
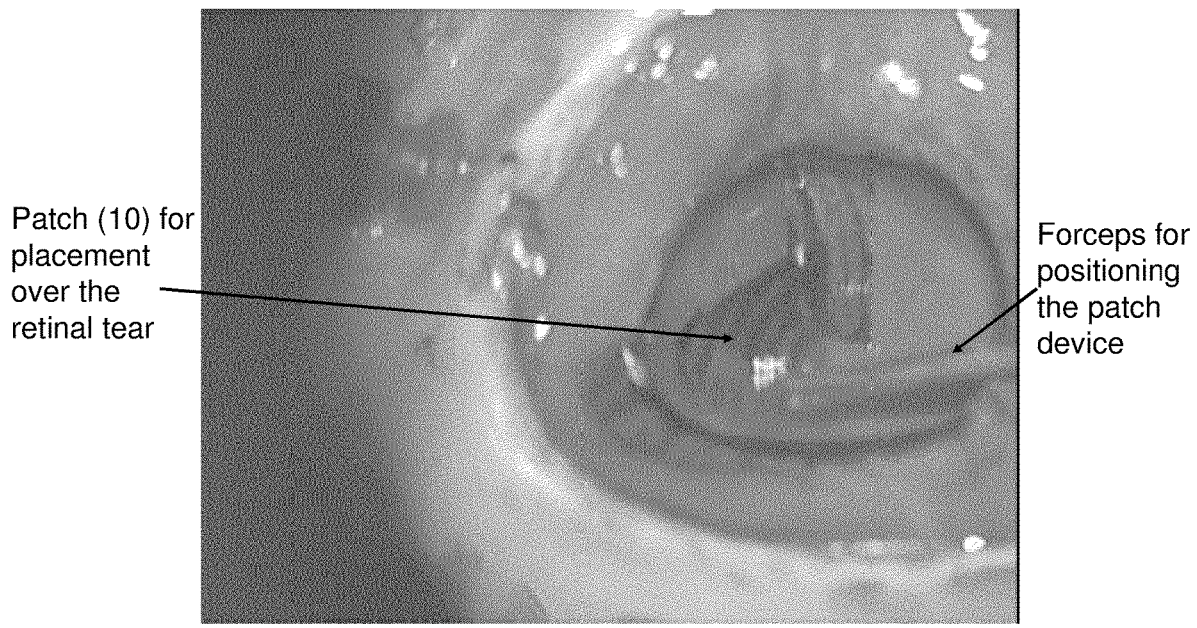
FIG. 6 is a photograph depicting experimental placement of a retinal patch over a retinal tear in a cadaver porcine eye, wherein the cornea was removed to expose the retina.
Figure 7:
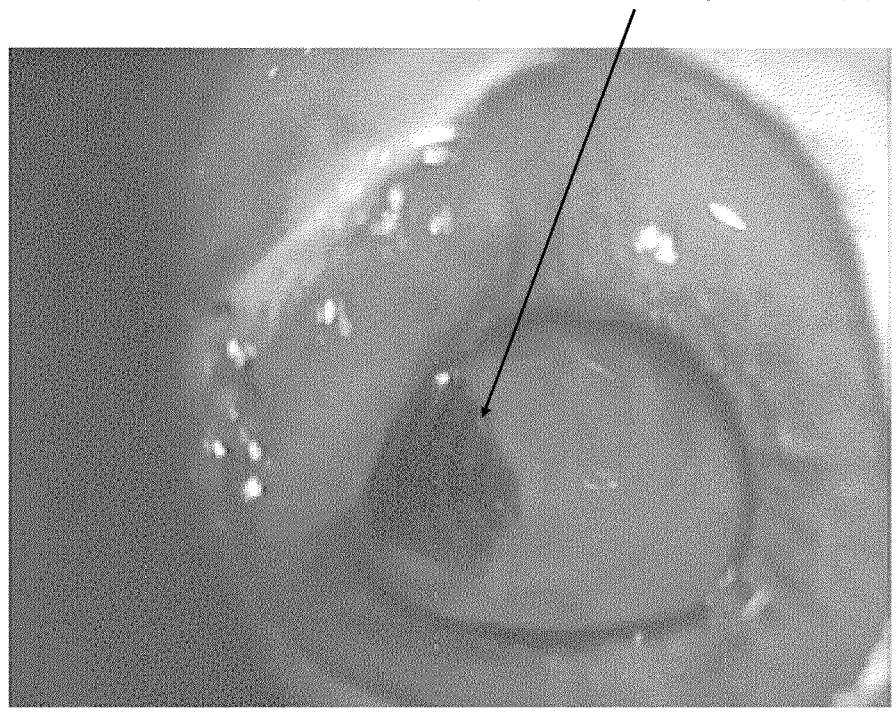
FIG. 7 is a photograph of an experiment depicting implantation of a retinal patch attached or adhered to a retinal tear in accordance with several embodiments disclosed herein.

An observational case-control trial was performed using 3 groups, each group comprising eight eyes. Group 1 included pig eyes, in which an open sky vitrectomy was done (see e.g., FIGS. 5-7; involving the removal of the cornea to expose the retina, though in surgical patients, traditional vitrectomy approaches are used), with the application of a silicone/disintegrin and a parylene C/disintegrin patch (See the placement schematic shown in FIG. 3). The disintegrin used in this experiment was vicrostatin (VCN) with a concentration of 100 M/L. The open sky approach allows the patch to be subjected to the same type of currents and fluid flow that would be experienced during a vitrectomy procedure (e.g., in order to maintain pressure in the eye). In Group 2 a closed 20 G pars plana vitrectomy was performed, with the application of both patch types (see, e.g., FIGS. 6 and 7). Group 3 involved a closed 20 G pars plana vitrectomy was done with the application of non-seeded disintegrin patches (silicone and parylene c). All eyes underwent exposure to mechanical forces to imitate the circumstances that usually accompanies a vitrectomy.

In Group 1, silicone/disintegrins patches were found to lift from the retinal surface, suggesting inadequate attachment was seen. However, in 6 of 8 parylene c/disintegrin patches remained adhered until direct pulling forces were applied.

In Group 2, silicone/disintegrins patches failed to attach to the retinal surface. However, 5 of 8 parylene C/disintegrins patches stayed in place till direct pulling forces were applied.

In Group 3, silicone patches did not attach to the surface, however all parylene patches adhered. Adherence was disrupted with application of indirect forces (e.g., water turbulence, subretinal solution currents, and subretinal blebs).

Thus in several embodiments, parylene patches are preferred for their adherence characteristics. However, in several embodiments silicone patches (or other polymers) are used, optionally with modification to the application/implantation process to improve adherence.

Example 4

Evaluation of Retinal Patch in Rabbit Eyes

Experiments to evaluate the use of disintegrins as adhesives as described in Example 3 were also performed on rabbits. Two (2) New Zealand rabbits were used in the study. The surgical procedures involved removing the vitreous, creating a 1-2 mm tear by vitrectomy, applying a parylene C/disintegrin patch and a control patch comprised of parylene C without disintegrins. FIGS. 8A-8C show images taken during the procedure of applying a parylene C/disintegrin patch. The patch exhibited obvious attachment to the retina, while the laser-ablated parylene C patch without disintegrins did not attach to the retinal surface and was easily lift by an intraocular gripping forceps.

Example 5

A composition comprising an adhesive is injected into the subretinal space surrounding a tear. Upon injection, the adhesive adheres to the site of the tear as well as to the available subretinal tissue, immobilizing the tear in a manner sufficient to facilitate healing.

Example 6

A composition comprising a disintegrin attached to a long chain polymer is injected into the subretinal space surrounding a tear. Upon injection, the disintegrin adheres to the site of the tear as well as to the available subretinal tissue, where self-association of the attached polymer chains assembles a patch, immobilizing the tear in a manner sufficient to facilitate healing.

Example 7

A composition comprising multiple disintegrin moieties attached at either end of a polymer chain such that a substantial fraction of polymer molecules have at least one disintegrin moiety attached at each end, is injected into the subretinal space surrounding a tear. Upon injection, the disintegrin moieties adhere to the site of the tear as well as to the available subretinal tissue, linking the two tissue layers together and thus immobilizing the tear in a manner sufficient to facilitate healing.

All publications, patents, patent applications, internet sites, and accession numbers/database sequences (including both polynucleotide and polypeptide sequences) cited are herein incorporated by reference in their entirety for all purposes to the same extent as if each individual publication, patent, patent application, internet site, or accession number/database sequence were specifically and individually indicated to be so incorporated by reference.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "implanting a polymeric patch" include "instructing the implantation of a polymeric patch."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately"

include the recited numbers. For example, "about 10 nanometers" includes "10 nanometers."

What is claimed is:

1. A patch configured to repair damaged ocular tissue, comprising:
a polymer matrix comprising parylene-C and having a first substantially planar surface and a second substantially planar surface;
a first adhesive component disposed over the first substantially planar surface; and
a second adhesive component disposed over the second substantially planar surface,
wherein the first adhesive component comprises a plurality of disintegrins coupled with at least a portion of the first substantially planar surface of the polymer matrix;
wherein the patch is configured to be positioned between two tissue layers of an eye in a subject during surgical implantation to adhere the two tissue layers together,
wherein retinal damage comprises a retinal tear, hole, dialyses, or detachment, and
wherein positioning of the patch over or adjacent to the retinal damage comprises placing the first adhesive component in contact with a retina in a damaged region, wherein the patch stabilizes the retinal damage and initiates repair of damaged ocular tissue.

2. The patch of claim 1, wherein the retinal damage comprises retinal detachment and wherein the patch is configured for implantation into subretinal space to reattach the retina to a choroid.

3. The patch of claim 2, wherein the plurality of disintegrins exhibit high affinity for integrin subunits such as αIIb, αv, α5, β1, β3 and β5.

4. The patch of claim 1 wherein the second adhesive component comprises a disintegrin, fibronectin, laminin, collagen, vitronectin or elastin.

5. The patch of claim 1, wherein the patch is fenestrated to facilitate oxygen and nutrient passage through the patch.

6. The patch of claim 1, wherein the disintegrins comprise vicrostatin, contortrostatin, ADAM derived polypeptides, or combinations thereof.

7. A biocompatible patch, comprising:
a polymer matrix having a first substantially planar surface and a second substantially planar surface;
a first adhesive component disposed over the first substantially planar surface; and
a second adhesive component disposed over the second substantially planar surface,
wherein the first adhesive component and the second adhesive component are configured for surgical implantation between two tissue layers of an eye in a subject to adhere the two layers together.

8. The patch of claim 7 wherein the patch is configured for surgical implantation on ocular tissues, to adhere to ocular tears/breaks, or to reattach a retina to a posterior wall of a subject's eye.

9. The patch of claim 7, wherein the polymer matrix is selected from the group consisting of polyimide, silicone, and parylene.

10. The patch of claim 9, wherein the polymer matrix comprises parylene-C.

11. The patch of claim 7, wherein the polymer matrix is a bio-erodible polymer selected from the group consisting of poly(caprolactone), poly(lactic acid), poly(glycolic acid), polyglactin, poly(lactic-co-glycolic acid), starch and collagen.

12. The patch of claim 7, wherein the first adhesive component is a same type as, or optionally a different type from the second adhesive component.

13. The patch of claim 7, wherein the first adhesive component, the second adhesive component, or both the first and second adhesive components comprise a reverse thermal polymer.

14. The patch of claim 13, wherein the reverse thermal polymer comprises pNIPAM.

15. The patch of claim 7, wherein the first adhesive component, the second adhesive component, or both the first and second adhesive components comprise a disintegrin, fibronectin, laminin, collagen, vitronectin or elastin.

16. The patch of claim 15, wherein the first adhesive component and/or the second adhesive component comprises disintegrin, vicrostatin, contortrostatin, or ADAM derived polypeptides.

17. The patch of claim 15, wherein the first adhesive component and/or the second adhesive component can be cleaved by one or more enzymes, wherein the one or more enzymes are selected from the group consisting of elastase, urokinase, plasmin and tissue plasminogen activator.

18. The patch of claim 7, wherein the patch is configured for temporary attachment or optionally for permanent attachment.

19. The patch of claim 7, wherein the patch, the first adhesive component, and the second adhesive component are configured for surgical implantation on ocular tissue, the ocular tissue being cornea, sclera, lens or retina.

20. The patch of claim 7, wherein the first adhesive component, the second adhesive component, and the polymer matrix are the same type of adhesive, and wherein the polymer matrix self-assembles in situ.

21. The patch of claim 7 wherein the first adhesive component and the second adhesive component are absent from a portion of the polymer matrix so that the first adhesive component and the second adhesive component are configured to make contact with tissue surrounding a treatment site, without contacting an injury.

22. The patch of claim 7 wherein the first adhesive component and/or the second adhesive component are a polymeric adhesive.

23. The patch of claim 7 wherein the first adhesive component and/or the second adhesive component are poly (N-isopropylacrylamide).

* * * * *

UNITED STATES PATENT AND TRADEMARK OFFICE
CERTIFICATE OF CORRECTION

PATENT NO. : 10,849,788 B2
APPLICATION NO. : 15/074909
DATED : December 1, 2020
INVENTOR(S) : Humayun et al.

Page 1 of 1

It is certified that error appears in the above-identified patent and that said Letters Patent is hereby corrected as shown below:

In the Specification

Column 1, Line 14:
After "FEDERAL FUNDING",
Delete:
"Certain embodiments of the inventions disclosed herein were funded, at least in part, by National Science Foundation Grant No. NSF ERC EEC-0310723. The Federal Government may have certain rights in various embodiments of the inventions disclosed herein."
And Insert:
--This invention was made with government support under EEC0310723 awarded by the National Science Foundation. The government has certain rights in the invention.--

Signed and Sealed this
Fifteenth Day of April, 2025

Coke Morgan Stewart
*Acting Director of the United States Patent and Trademark Office*